US008535500B2

(12) United States Patent
Lee et al.

(10) Patent No.: US 8,535,500 B2
(45) Date of Patent: Sep. 17, 2013

(54) SURFACE ACOUSTIC WAVE SENSOR DEVICE INCLUDING TARGET BIOMOLECULE ISOLATION COMPONENT

(75) Inventors: Hun Joo Lee, Hwaseong-si (KR); Soo Suk Lee, Suwon-si (KR); Mi Jeong Song, Suwon-si (KR); Kyung Yeon Han, Seoul (KR); Jae Ho Kim, Suwon-si (KR)

(73) Assignees: Samsung Electronics Co., Ltd., Suwon-si (KR); Ajou University Industry-Academic Cooperation Foundation, Suwon-si (KR)

(*) Notice: Subject to any disclaimer, the term of this patent is extended or adjusted under 35 U.S.C. 154(b) by 237 days.

(21) Appl. No.: 12/974,761

(22) Filed: Dec. 21, 2010

(65) Prior Publication Data
US 2012/0000779 A1 Jan. 5, 2012

(30) Foreign Application Priority Data
May 3, 2010 (KR) .................. 10-2010-0041383

(51) Int. Cl.
*G01N 27/447* (2006.01)
*G01N 27/453* (2006.01)

(52) U.S. Cl.
USPC ........... 204/450; 204/451; 204/456; 204/414; 204/601; 204/606; 435/173.9; 210/748.02

(58) Field of Classification Search
USPC .................. 204/403.01, 414, 450, 456, 548, 204/549, 600, 601, 606, 644, 645; 205/777.5, 205/792; 137/565.11; 422/505, 507; 435/173.9; 210/748.01, 748.02
See application file for complete search history.

(56) References Cited

U.S. PATENT DOCUMENTS

| 2002/0040275 A1* | 4/2002 | Cravatt et al. ................ 702/19 |
| 2003/0226755 A1* | 12/2003 | Ramsey ..................... 204/600 |
| 2004/0072208 A1* | 4/2004 | Warthoe et al. ................ 435/6 |
| 2004/0115709 A1* | 6/2004 | Morozov et al. ................ 435/6 |
| 2007/0281369 A1 | 12/2007 | Carter et al. |

FOREIGN PATENT DOCUMENTS

| KR | 1020030079468 A | 10/2003 |
| KR | 1020040068364 A | 7/2004 |
| KR | 1020090047968 A | 5/2009 |

* cited by examiner

*Primary Examiner* — Keith Hendricks
*Assistant Examiner* — Susan D Leong
(74) *Attorney, Agent, or Firm* — Leydig, Voit & Mayer, Ltd.

(57) ABSTRACT

Provided herein is a surface acoustic wave ("SAW") sensor device including an isolation component of a target biomolecule. A sample containing the target biomolecule is separated by its size using electrophoresis, and sequentially reacts with a SAW sensor. In other words, the device is capable of detecting the target biomolecule by separating biomolecules using electrophoresis, and applying the separated biomolecules to the SAW sensor.

18 Claims, 5 Drawing Sheets

SURFACE ACOUSTIC WAVE SENSOR DEVICE INCLUDING TARGET BIOMOLECULE ISOLATION COMPONENT

CROSS-REFERENCE TO RELATED APPLICATIONS

This application claims priority to Korean Patent Application No. 10-2010-0041383, filed on May 3, 2010, and all the benefits accruing therefrom under 35 U.S.C. §119, the content of which in its entirety is herein incorporated by reference as if fully set forth herein.

BACKGROUND

1) Field

Provided is a surface acoustic wave sensor device including a target biomolecule isolation component, and a method of detecting a target biomolecule.

2) Description of the Related Art

A surface acoustic wave ("SAW") is a mechanical wave (in contrast to an electrical wave) that is generated from the movement of particles due to external thermal, mechanical, and/or electrical forces. In a SAW, a large portion of vibrational energy is concentrated on the surface of a medium. A SAW sensor is a device sensing the presence or properties of a target material using a SAW.

The SAW sensor is disposed on a substrate formed of a piezoelectric material and includes a receptor specifically binding to a desired target material on the surface. Thus, when a solution containing the target material flows to the SAW sensor, a wavelength is changed due to a physical, chemical and/or electrical reaction between the target material and the receptor. Such a change leads to a signal change, which is used to determine and/or monitor the content of the target material.

A biosensor detects bioproducts such as biomolecules including proteins, deoxyribonucleic acid ("DNA"), bacteria, animal cells, tissues, etc., and toxins produced thereby. As the biomolecules specifically bind to a surface of the sensor, a surface mass of the sensor is changed, leading to a signal change in the sensor. Here, the sensor is very sensitive to pressure of a fluid, and viscosity and density of a medium, as well as the change in surface mass.

A resonance and oscillation device to generate a wave of the SAW device may use an oscillation method of applying an output signal from the SAW device to an input signal of the SAW device to check a wave change of the SAW device, or a method of generating a specific frequency outside the SAW device, applying the frequency to an input inter-digital transducer ("IDT") electrode of the SAW device, and plotting the output signal according to each frequency.

SUMMARY

Provided is a surface acoustic wave ("SAW") sensor device including an isolation component for separating (i) a biomolecule having a size the same as or similar to a target biomolecule or (ii) a biomolecule having a size considerably different from the target biomolecule by using an electrophoresis, and a SAW sensor having a receptor specifically binding to the target biomolecule.

In embodiments, any type of electrophoresis which enables separation of biomolecules by their size may be used, which may include, but is not limited to, gel electrophoresis, capillary electrophoresis, isoelectric focusing electrophoresis, and isotachophoresis.

In one embodiment, the isolation component may include a first chamber containing a first buffer and in which a first electrode contacts the first buffer, a second chamber containing a second buffer and in which a second electrode contacts the second buffer, a channel connecting the first chamber to the second chamber, a blocking wall disposed at an end of at least one of the channels of the first and second chambers, a sample chamber disposed at an entry of the channel and into which a sample is loaded, and a third chamber disposed at an exit of the channel and to which a biomolecule passed through the channel is transferred. The SAW sensor may be connected to the third chamber.

In an embodiment, one or more channels may be used, and the channel may be a gel tube or a capillary filled with electrophoresis gels. The plurality of channels may be the same as or different from each other. Here, the channels may differ in at least one of the kind of a sample, the size and length of the channel, the composition and concentration of the gel, and a coating material for the channel.

In an embodiment, the SAW sensor device may further include an upper channel and a lower channel disposed on and under the third chamber. At the lower channel, the SAW sensor may be disposed, and at the upper channel, a disposal chamber may be disposed. Pumps may be disposed at ends of the upper channel and/or the lower channel.

In an embodiment, the SAW sensor may include a piezoelectric substrate, a pair of inter-digital transducer ("IDT") electrodes disposed on the substrate, and a reactive layer disposed on the piezoelectric substrate to cover the IDT electrodes and including the receptor specifically binding to the target biomolecule.

In an embodiment, an electric sensor sensing biomolecules may be disposed at the third chamber.

In an embodiment, the blocking wall may include a material passing a current, but not passing ions and/or gases generated from a buffer.

Provided is a method of detecting a target biomolecule, the method including separating biomolecules having a size the same as or similar to the target biomolecule or separating biomolecules excluding biomolecules having a size considerably different from the target material from a sample, and reacting the separated target biomolecule with a reaction part on a surface of the SAW sensor including a receptor specifically binding to the target biomolecule.

In an embodiment, the separation of the biomolecules may be performed by an electrophoresis.

In an embodiment, such detection of the target material may be performed using the SAW sensor device described above.

BRIEF DESCRIPTION OF THE DRAWINGS

The above and other aspects of the invention will become more readily apparent by describing in further detail embodiments thereof which reference to the accompanying drawings, in which.

DETAILED DESCRIPTION

The invention now will be described more fully hereinafter with reference to the accompanying drawings, in which a non-limiting embodiment is shown. This invention may, however, may be embodied in many different forms, and should not be construed as limited to the embodiments set forth herein. Rather, these embodiments are provided so that this disclosure will be thorough and complete, and will fully convey the scope of the invention to those of ordinary skill in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer, or section from another element, component, region, layer or section. Thus, a first element, component, region, layer, or section discussed below could be termed a second element, component, region, layer, or section without departing from the teachings of the present invention.

Spatially relative terms, such as "lower," "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprises" and/or "comprising," or "includes" and/or "including" when used in this specification, specify the presence of stated regions, integers, steps, operations, elements, and/or components, but do not preclude the presence or addition of one or more other regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, the present invention will be described in detail with reference to the accompanying drawings.

In an embodiment, a surface acoustic wave (hereinafter, referred to as a "SAW") sensor device capable of detecting a target biomolecule using as a SAW sensor is provided. The SAW sensor has a receptor fixed on a surface to specifically bind to a target biomolecule. When the target biomolecule present in a sample binds to the receptor, a surface mass density is increased and thus the speed of the SAW is decreased. Due to such a change in the speed, the target biomolecule can be qualitatively and quantitatively analyzed.

However, when other materials in the sample excluding the target biomolecule non-specifically bind to the surface of the SAW sensor, the SAW speed is changed, causing a noise during a detecting process. In one embodiment, for example, since blood, which is commonly used as a sample, contains a large amount of antibodies, which serve as receptors, if the antibodies from the blood are not separated before use, a reaction between the receptor antibody and the target biomolecule on the surface of the SAW sensor is inhibited. When the sample contains large amounts of materials such as proteins, in addition to the receptor such as an antibody, the materials hinder dispersion of the target biomolecule, leading to a decrease in rate of binding of the target biomolecule with the SAW surface receptor.

To solve such a problem, a method of separating the target biomolecule using affinity chromatography using an antibody may be used. However, this method requires use of a solution decreasing the affinity of an antibody by reducing pH or changing the concentration of ions for re-separation from the antibody fixed to a column. The solution inhibits the bonding strength between the separated target biomolecule and the antibody on the surface of the SAW sensor to reduce the sensitivity of the SAW sensor.

Thus, a sensor device in which a target biomolecule in the sample is separated from a large amount of other materials and applied to the SAW sensor using an electrophoresis is provided. Electrophoresis uses a principle of moving ionic materials in a specific direction at a specific rate according to the charge and mobility of the materials, when an electric field is applied to the ionic materials. Electrophoresis is a technique of separating ionic materials by surface charge characteristics according to the target biomolecules size, shape, and average charge, and a mobility difference according to the pH, concentration, and temperature of an aqueous solution. Accordingly, the size of the biomolecule is inversely proportional to the logarithmic function of the mobility of the biomolecule in the electric field. Therefore, since the biomolecule is purely separated by its size, a subsequent process is not needed.

In an embodiment, as a sensor for detecting a target biomolecule in a sample, a SAW sensor device in which an isolation component separating a biomolecule having a size the same as or similar to the target biomolecule or a biomolecule having a size considerably different from the target biomolecule by means of an electrophoresis, is integrated with a SAW sensor having a receptor specifically binding to the target biomolecule is provided. In other words, the SAW sensor may detect the target biomolecule by primarily grouping or separating various biomolecules in a sample by size, and secondarily separating the separated biomolecules, that is, biomolecules having a size approximately similar to or not considerably different from the target biomolecule, using an electrophoresis apparatus.

The separation using electrophoresis occurs due to a difference in migration rate according to the properties of particles such as structures or sizes of sample components, which are different from each other in the electric field.

The sample may migrate through a membrane or gel as a supporting structure during gel electrophoresis. The supporting structure may include, but is not limited to, a filter, acetic acid cellulose, an agarose gel, a starch gel, or an acrylamide gel.

A filter is a supporting structure which is cheap and convenient to use. However, since materials to be separated are easily adsorbed to cellulose, a boundary between bands of the electrophoresis is not clear.

Acetic acid cellulose is made by acetylating a hydroxyl group of the acetic acid cellulose. It is short in separation time, convenient in detection and easily dissolved in various solvents, and thus can be rapidly and easily recovered.

An agarose gel is suitable for measurement using a photometer and easy to use due to its transparency. Particularly, it is mainly used in immunoelectrophoresis using a slide, and agarose obtained by removing agaropectin from an agar gel is useful in separating deoxyribonucleic acid ("DNA"), ribonucleic acid ("RNA") and plasmids.

The pore size of a starch gel is determined by the kind of starch, the kind of a buffer and pH, and serves as a sieve for screening molecules. The starch gel is widely used to separate several isoenzymes.

In the case of an acrylamide gel, two types of acrylamide gels having different network structures are stacked to form a discontinuous layer. In this case, a pore size of the network structure of the supporting structure may be changed by changing the concentration of acrylamide. The upper gel, which is less dense, is a stacking gel serving to concentrate charged particles such as proteins. For this reason, a sample passing through this gel forms a clear band. The acrylamide gel is capable of separating molecules according to the charges of components or their masses alone. The acrylamide gel is used in protein separation, examination of the purity of a purified protein, measurement of the molecular weight of a protein, and determination of DNA base sequence. By using the acrylamide gel, a small amount of a sample mixture can be separated in a short time.

Gel electrophoresis refers to electrophoresis using a gel as a supporting structure. In an alternative embodiment, when a sample is shown as a band, it is referred to as zone electrophoresis. As molecules having the same size migrate as a group, they are shown as a single band in electrophoresis. Since a smaller molecule migrates faster than a larger molecule, the molecules having different sizes are shown as bands at different locations. The sizes of the molecules shown as the respective bands may be determined by comparing relative locations of the bands shown on the gel by the electrophoresis.

In another alternative embodiment, there is a method which is referred to as disc electrophoresis. The disc electrophoresis is a transformed method of the zone electrophoresis, which can separate charged particles such as proteins into very clear bands using an acrylamide gel. Compared to the zone electrophoresis, the disc electrophoresis uses two kinds of gels and different buffering systems used in a gel supporting structure and a buffer tank. This method is called disc gel electrophoresis because of discontinuity of the hydrogen ion concentration, ion intensity, composition of the buffer and gel concentration in the two gel systems. According to this acrylamide electrophoresis, even a single base pair difference can be detected because of high resolution, a large amount of samples can be dealt with, and the sample material can be easily recovered from the gel.

In addition to the gel electrophoresis, there may be capillary electrophoresis, isoelectric focusing electrophoresis, and isotachophoresis.

The capillary electrophoresis may separate molecules by size using a capillary, and detect them using a detector. The capillary electrophoresis separation uses a capillary having an internal diameter of about 25 micrometers ($\mu$m) to about 75 $\mu$m, and can have a high theoretical plate of one hundred thousand or more under the influence of electroosmotic flow, which is an electrophoresis phenomenon. The capillary electrophoresis may analyze all solutes at the same time with a high efficiency, a fast analyzing time, and even with small sample consumption, regardless of their charges. Therefore, the capillary electrophoresis is widely used in analyses of biological macromolecules, amino acids, chiral drugs, proteins, and carbohydrates. A wall of the capillary is modified or coated with an inactive material such as polyacrylamide or poly(vinyl-pyrrolidinone).

The isoelectric focusing electrophoresis uses a phenomenon in which charged components (e.g., proteins) are focused at a predetermined location in a supporting material. Amino acid, which is a component of a protein, has a specific charge by residue in an aqueous solution. Therefore, the protein, a polymer of these amino acids, has charges derived from the amino acids. These charges change with the pH of the aqueous solution. A positive charge or negative charge is neutralized. Accordingly, when the protein mixture is loaded on a gel that is in the pH gradient and an electric field is applied, due to its charge, it migrates toward an opposite charge and thus the pH is changed, leading to gradual migration toward a neutral charge. At the neutral charge location, a net charge is 0, and the migration of the protein stops. The isoelectric focusing electrophoresis separates a protein by isoelectric point using the above-described principle.

The isotachophoresis stands out among electrophoresis because there is no supporting material in an electrolyte to remove a convention current. However, as the separation is performed in a capillary, dispersion is reduced. Furthermore, dilution effects caused by electrophoresis migration of buffer ions passing thorough sample sections are removed by using two very different buffer ions. While a buffer solution in a leading part contains ions having a higher mobility than ions in the sample, a buffer solution in a terminating part contains ions having a lower mobility than the ions in the sample. Therefore, the disturbance of the ions in the sample because of the buffer ions does not occur. Each section is detected using a potential gradient detector sensing a local change occurring in an electric field when an ultraviolet ray is absorbed or the ions pass through the sample section. This technique may be widely applied in small organic and inorganic ions, such as inorganic materials ($NO_3^-$ or $SO_4^{2-}$) in water waste or amino acids and organic acids in wine, fruit juice and a physiological sample.

However, when a conventional electrophoresis apparatus is used, a sample or separated target biomolecule may be diluted by a buffer for delivering a current.

For this reason, in the illustrated embodiments, a buffer chamber and a sample chamber are separated to protect a sample from ions generated in the buffer chamber during current application without dilution of the sample or separated target biomolecule.

Figure 1:
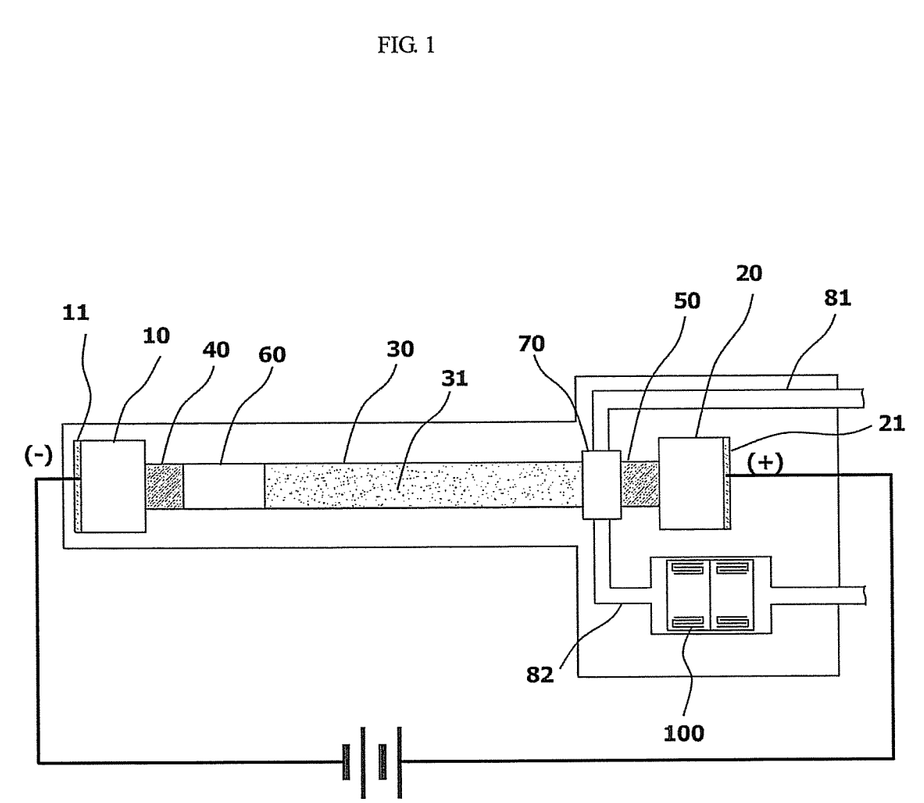
FIG. 1 is a diagram of an embodiment of a surface acoustic wave ("SAW") sensor device, according to the invention.
Figure 2:
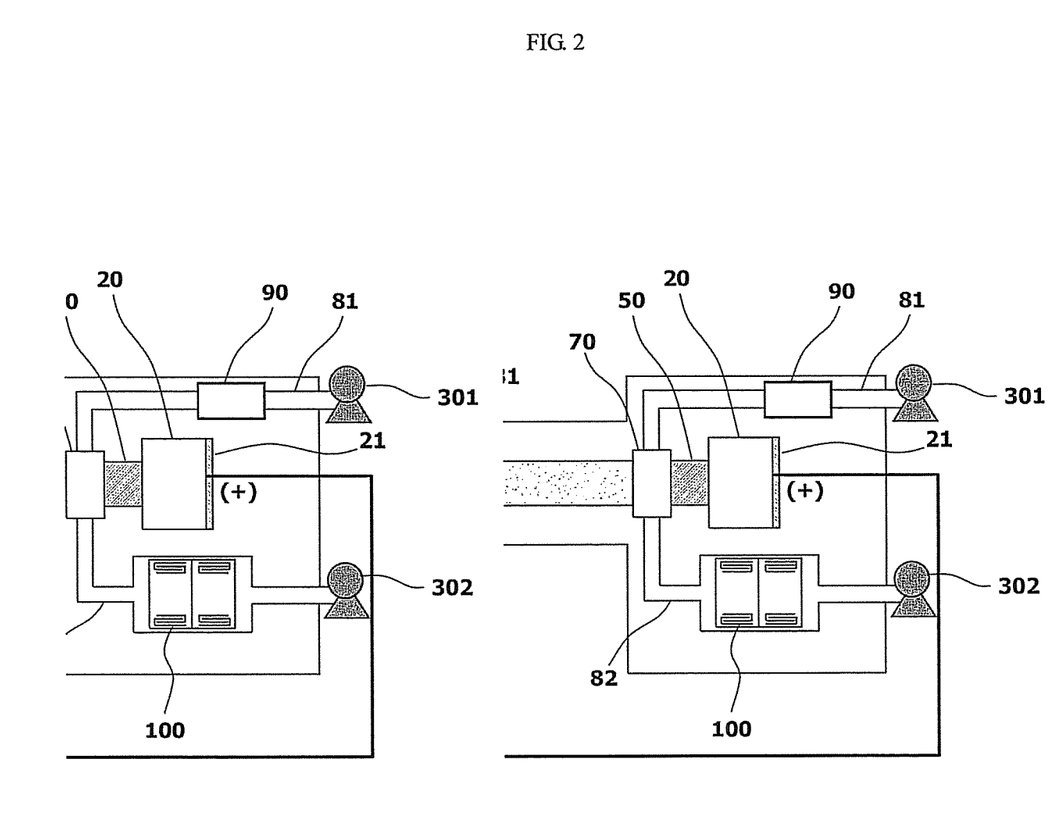
FIG. 2 is a schematic diagram of another embodiment of a SAW sensor device, according to the invention.

FIGS. 1 and 2 schematically illustrate an embodiment of a SAW sensor device according to the invention.

Referring to FIG. 1, a channel chamber 30 forming a channel 31 therein is disposed between a first chamber 10 and a second chamber 20, and these components form a part of an electrophoresis apparatus in the SAW sensor device. The SAW sensor device includes a SAW sensor 100 to detect a target biomolecule from a sample which has been subjected to electrophoresis in the electrophoresis apparatus. A sample may include a target molecule, a biomolecule having a similar size to the target biomolecule and a biomolecule having a different size.

Such a sensor device primarily separates or groups the biomolecule having a similar size to the target biomolecule, or primarily separates or groups the biomolecule having a considerably different size from the target biomolecule, from the sample through electrophoresis. Afterwards, a separated biomolecule is transferred to the SAW sensor 100. In the former case, the separated biomolecule having a similar size to the target biomolecule is transferred to the SAW sensor 100, and in the latter case, biomolecules remaining after the separation (e.g., the separated biomolecule having a similar size to the target biomolecule) is transferred to the SAW sensor 100.

Therefore, the SAW sensor 100 may reduce errors caused by non-specific bindings, and be increased in sensitivity and reproducibility. As a large amount of reaction inhibitors (e.g., antibodies) in the sample are removed, a reaction rate on a surface of the SAW sensor 100 may be increased, leading to the improvement in sensitivity. Furthermore, since an electrophoresis is used to primarily separate the target biomolecule, the intact sample can be isolated, and the process can be performed at a low cost since it does not use an expensive antibody. Since a re-separation process for the target biomolecule is not necessary in a subsequent process after the separation, the SAW sensing can be performed with high sensitivity without sensitivity loss, and the separation can be performed in a simple and rapid process.

The first chamber 10 and the second chamber 20 contain a first buffer and a second buffer, respectively. A first electrode 11 and a second electrode 21 are in the first chamber 10 and the second chamber 20, and contact the first buffer and the second buffer, respectively.

The channel chamber 30 serves to connect (e.g., fluidly) the first and second chambers 10 and 20 to each other. The channel 30 chamber may be a gel tube or capillary, which is filled with electrophoresis gels. The capillary may or may not be filled with electrophoresis gels. The component of the electrophoresis gel or the size of the capillary may be varied according to the kind of the target biomolecule to be processed within the SAW sensor device. The electrophoresis gel may be an agarose gel, a starch gel or an acrylamide gel. For DNA or RNA analysis, an agarose gel is mainly used, and for protein analysis, a polyacrylamide gel is mainly used.

In an embodiment of the invention, a single channel chamber 30 with a single chamber 31, or a plurality of the channel chamber 30 and/or channels 31 may be used. The plurality of channel chambers 30 may be the same as or different from each other. When the plurality of channel chambers 30 are all different, at least one selected from the group consisting of the kind of the sample, the size and length of the channel chamber 30, the composition (e.g., kind) of the gel, the concentration (e.g., contents) of the gel, and the coating material for the channel chamber 30 may differ for each channel, to increase a separation ratio. The use of the different kind of sample indicates that a different sample is input into each channel chamber 30. When the channel chambers 30 are capillaries, they may be varied in characteristics such as the size, internal coating, and length of the capillary. The plurality of channel chambers 30 may be included in the form of an array or cartridge.

A sample chamber 60 into which a sample is loaded is disposed between the first chamber 10, which is at an entry of the channel chamber 30, and the channel chamber 30. A third chamber 70 to which the biomolecule passing through the channel 30 is transferred, is disposed between the channel chamber 30 at an exit of the channel chamber 30, and the second chamber 20. Accordingly, when the sample is loaded into the sample chamber 60 and electricity flows, biomolecules in the sample migrate to the channel 31. Then, the biomolecules passing through the channel chamber 30 migrate to the third chamber 70.

Blocking walls 40 and 50 preventing the buffer from flowing out from the buffer chambers 10 and 20, respectively, are disposed at ends of the channel chamber 30. The blocking walls 40 and 50 are disposed at respective sides of the first and second chambers 10 and 20, so as to be between the first chamber 10 and the channel chamber 30, and between the second chamber 20 and the channel chamber 30 as illustrated in FIG. 1. The blocking walls 40 and 50 serve to prevent the dilution of the sample, and thus may be disposed at a first end of the channel chamber 30 disposed at an inner side of the second chamber 20, and at a second end of the channel chamber 30 opposite the first end disposed at an inner side of the first chamber 10, to prevent flow of the diluted sample into the SAW sensor 100.

In other words, to separate the sample chamber 60 from the buffer chamber (e.g., the first chamber 10), the first blocking wall 40 is disposed between the sample chamber 60 and the first chamber 10, and the second blocking wall 50 is disposed between the third chamber 70 to which the biomolecules passing through the channel chamber 30 are transferred and the buffer chamber (e.g., second chamber 20) for such a reason. Due to the blocking walls 40 and 50, dilution of the sample or the separated target biomolecule by the buffer can be reduced or effectively prevented. In addition, the sample can be protected from ions generated in the buffer chambers when a current for electrophoresis is applied.

The blocking walls 40 and 50 may pass the current, but may not pass the ions and/or gases generated from the buffer. In one embodiment, for example, the blocking walls 40 and 50 may pass electricity, but may not pass hydrogen ions and hydroxide ions and/or gases. Specifically, the blocking walls 40 and 50 may include, but are not limited to, Nafion™ (Dupont), Dowex™ (Aldrich) or Diaion™ (Aldrich) materials.

In such a structure, an electric field is formed by electrodes 11 and 21 respectively disposed at opposing ends of the channel 30, and charged particles are separated through the channel 30, which is a medium in the electric field, by their size and property. A process of separating biomolecules will be described. When voltages are applied to both ends of the channel 30, provided that a first buffer is set as a positive electrode, and a second buffer is set as a negative electrode, a voltage difference is created due to a gel or capillary of the channel 30 between the both buffers. Due to the voltage difference, positively-charged materials in the sample migrate to the negatively-charged second buffer, and negatively-charged materials in the sample migrate in the opposite direction. Here, each biomolecule of the sample has a different migration rate according to its characteristics such as a molecular weight, and thus may be separated from each other.

By the electrophoresis, a biomolecule capable of hindering the binding between the target biomolecule and a surface receptor of the SAW sensor 100 is previously separated from the sample to increase the detection sensitivity of the SAW sensor 100.

In one embodiment, if the sizes of the receptor and the target biomolecule are considerably different, and a biomolecule having a similar size to the receptor is included in the sample, it can be separated and removed. Biomolecules other than the biomolecules having a considerably different size from the target biomolecule may be transferred to the SAW sensor 100. In one embodiment, for example, the biomolecules having a size about ±500%, ±400%, ±300%, ±200% or ±100% or more of the target biomolecule may not migrate to the SAW sensor 100, but the invention is not limited to these numerical limits.

In another embodiment, the biomolecules having a size similar to the target biomolecule may be separated and transferred to the SAW sensor 100. In one embodiment, for example, only biomolecules having a size approximately ±50%, ±40%, ±30%, ±20% or ±10% or less of the target biomolecule may be transferred to the SAW sensor, but the invention is not limited to these numerical limits.

Among the biomolecules, the biomolecules having a size considerably different from the target biomolecule are not transferred to the SAW sensor 100 and need to be disposed of Referring to FIGS. 1 and 2, a disposal chamber 90 may be physically and fluidly connected to a side of the third chamber 70, which is not physically connected to the SAW sensor 100. As illustrated in FIG. 2, for example, the third chamber 70 and the disposal chamber 90 are both connected to an upper channel 81, and the third chamber 70 and the SAW sensor 100 are connected to a lower channel 82. The separated and removed biomolecules are transferred to the disposal chamber 90 in the SAW sensor devices shown in FIGS. 1 and 2. In the illustrated embodiments, the target biomolecule and the biomolecules other than the biomolecules having a size similar to (e.g., different from) the target biomolecule are transferred in different paths within the SAW sensor device.

The third chamber 70 is connected to the SAW sensor 100. To determine whether a sensed biomolecule reaching the third chamber 70 is transferred to the SAW sensor 100 or disposal chamber 90, an electric sensor (not shown) capable of sensing a biomolecule may be installed in or connected to the third chamber 70. One or more electric sensors may be used. In embodiments, the electric sensor may be disposed only on a side of the third chamber 70 facing the channel 30, or two electric sensors may be disposed where one is on a side of the third chamber 70 facing the upper channel 81 and one is on a side of the third chamber 70 facing the lower channel 82.

Referring to FIG. 2, pumps 301 and 302 are installed at the upper channel 81 and/or the lower channel 82 to provide transfer power for migration of the biomolecules. The pumps 301 and 302 increase or decrease a pressure according to the type of a positive or negative pressure.

Figure 3:
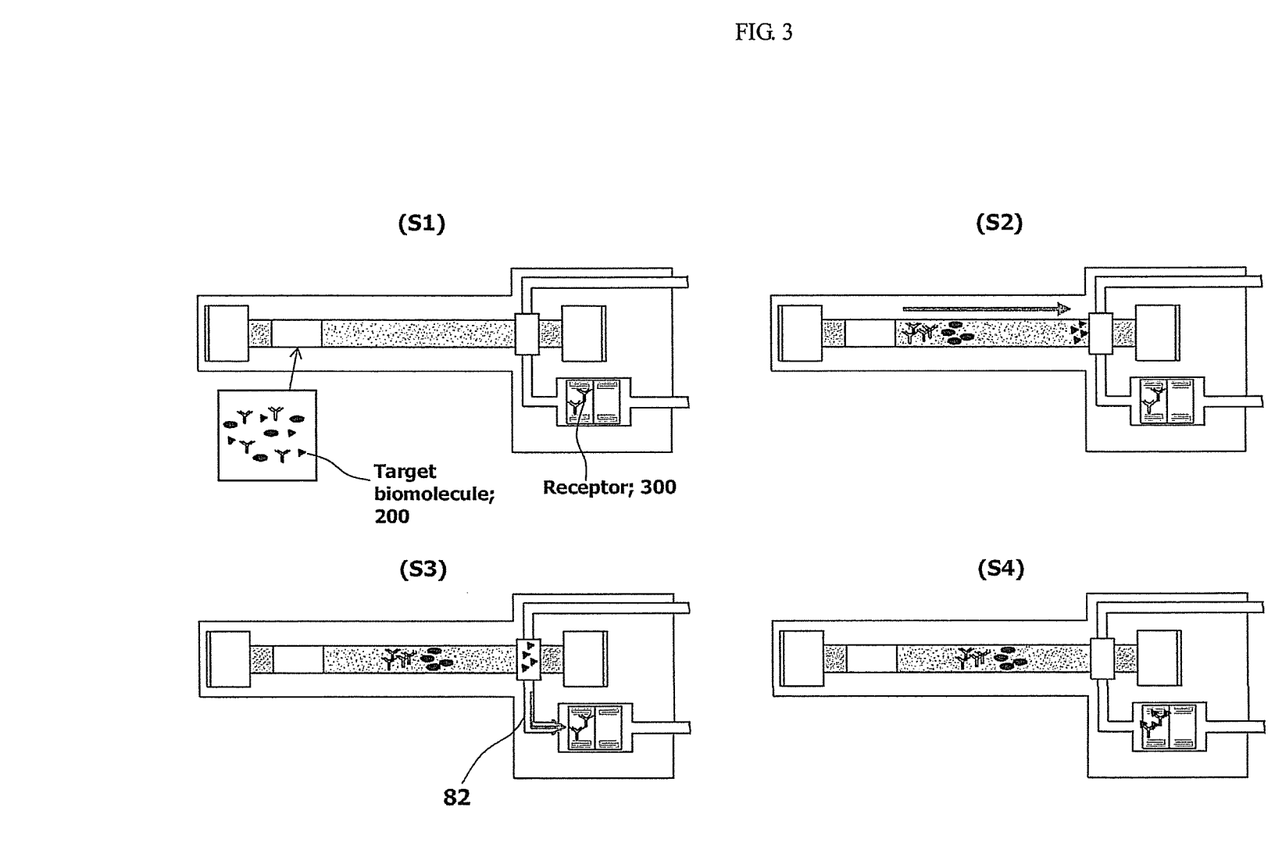
FIG. 3 is a schematic diagram illustrating an embodiment of a process of detecting a target biomolecule having a relatively small size.
Figure 4:
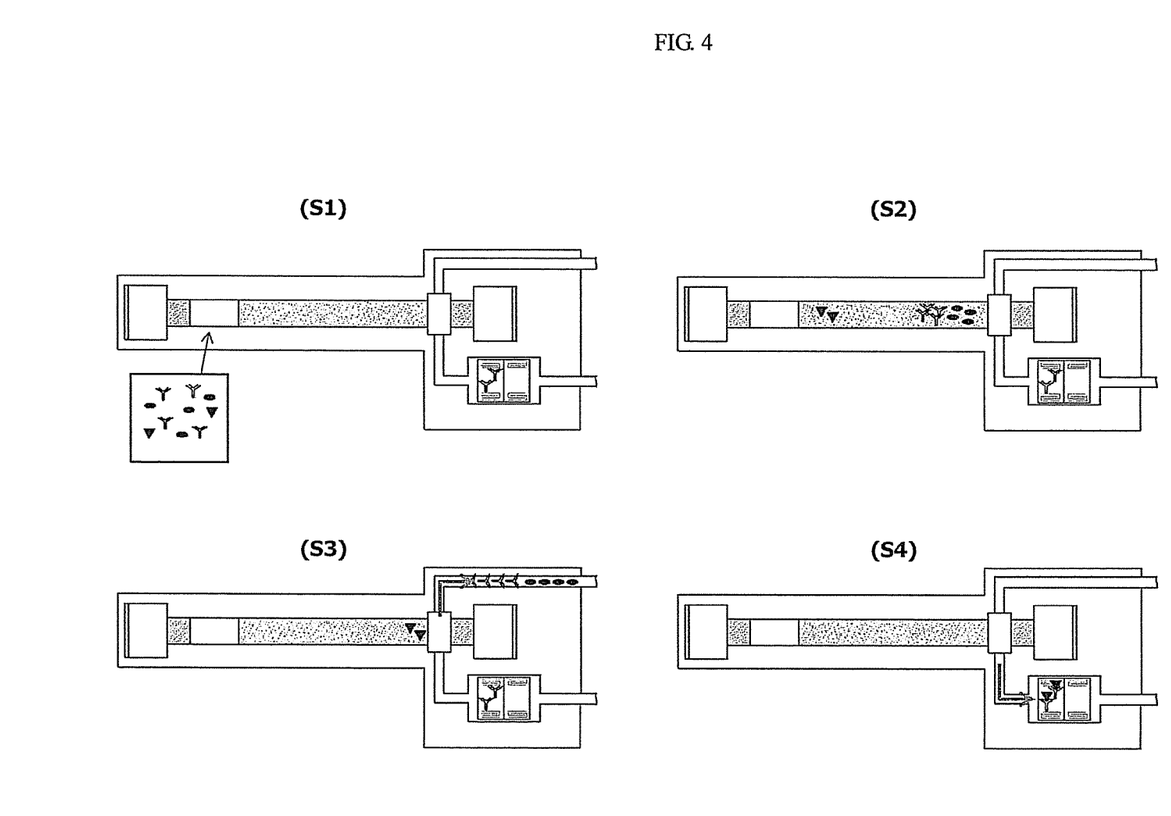
FIG. 4 is a schematic diagram illustrating an embodiment of a process of detecting a target biomolecule having a relatively large size.

FIGS. 3 and 4 schematically illustrate embodiments of a process of detecting a target biomolecule using a SAW sensor device according to the invention. In FIGS. 3 and 4, the reference lines and numerals indicating the elements corresponding to those in FIG. 1 will be omitted.

Referring to FIGS. 1 and 3, a process of detecting a target biomolecule having a relatively small size is provided. A sample including a target biomolecule 200, small biomolecules and large biomolecules, is loaded into a sample chamber 60, and a buffer is poured in first and second buffer chambers 10 and 20 (S1). When an electric current is applied to the first and second buffer chambers 10 and 20 using electrodes 11 and 21, a grouping or separation by size of the biomolecules of the sample is carried out in a channel 31 through electrophoresis (S2). Since a smaller biomolecule has a higher migration rate than a larger biomolecule, the smaller biomolecule migrates faster to an exiting end of the channel 31 adjacent to the third chamber 70, which is opposite to the entry end of the channel 31 adjacent to the sample chamber 60. When biomolecules corresponding to (e.g., similar to) the size of the target biomolecule 200 reach the third chamber 70, the electric current is interrupted to separate the target biomolecule 200 from the remaining small and large biomolecules (S3). The separated target biomolecules 200 from the original sample are transferred to the SAW sensor 100 through a lower channel 82 (S4). A receptor 300 is physically and/or electrically connected to a surface of the SAW sensor 100.

Referring to FIGS. 1 and 4, a process of detecting a target biomolecule having a large size is schematically illustrated. Unlike FIG. 3, when biomolecules having a small size reach the third chamber 70, the current is interrupted (S2), and the small-sized biomolecules are transferred to an upper channel 81 through the third chamber 70 (S3). Likewise, after the small-sized biomolecules are removed from the channel 31 to the upper channel 81, a current is applied again until the large-sized target biomolecules 200 reach the third chamber 70. Afterwards, the current is interrupted again, and the large-sized biomolecules are transferred to the upper channel 81 through the third chamber 70 (S3). Finally, the target biomolecules 200 are transferred to the SAW sensor 100 through the lower channel 82 (S4).

The SAW sensor 100 may convert a subtle change in mass caused by the interaction between molecules on its surface into a frequency shift (or phase shift) to detect them.

The SAW sensor 100 may be used to detect all materials having a mass, and when a material of the receptor 300 specifically binds to the surface of the SAW sensor 100, and thus a surface mass of the SAW sensor 100 is changed, the SAW sensor 100 can be changed in signal and thereby diagnose the presence and content of the target material (e.g., target biomolecules 200).

Figure 5:
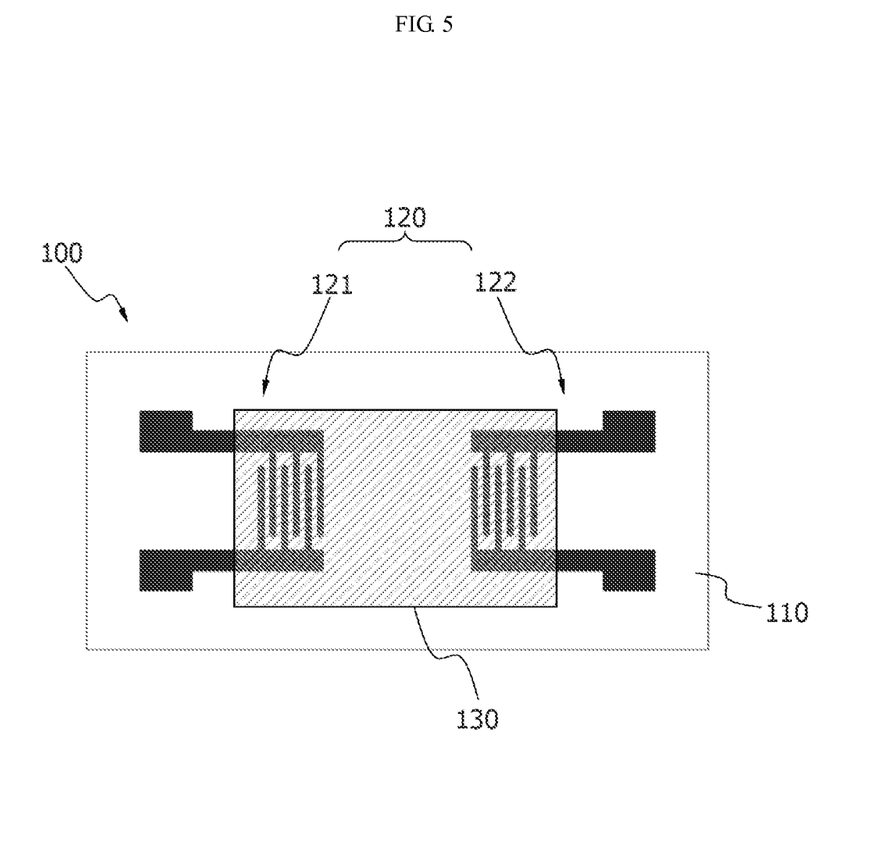
FIG. 5 is a schematic diagram of embodiment of a SAW sensor, according to the invention.

FIG. 5 schematically illustrates embodiment of the SAW sensor 100 according to the invention. Referring to FIG. 5, the SAW sensor 100 includes a piezoelectric substrate 110, a pair of inter-digital transducer ("IDT") electrodes 121 and 122 disposed on the substrate 110, and a reactive layer 130 disposed on the piezoelectric substrate 110. The electrodes 121 and 122 collectively form an IDT electrode 120. The reactive layer 130 covers (e.g., overlap) a portion of the IDT electrodes 121 and 122, and binds directly to a target material to be detected or includes a receptor 300 (of FIG. 3) which binds directly to the target material to be detected.

The receptor 300 of the reactive layer 130 is a material specifically binding to a target biomolecule. In one embodiment, for example, the receptor 300 may be an antibody.

A piezoelectric material of the substrate 100 is a material whose electrical characteristic is converted when a mechanical signal is applied (e.g., the piezoelectric effect), or generating a mechanical signal when an electrical signal is applied (e.g., the reverse piezoelectric effect). In one embodiment, for example, the piezoelectric material may include, but is not limited to, lithium niobate ($LiNbO_3$), lithium tantalite (LiTaO$_3$), lithium tetraborate (Li$_2$B$_4$O$_7$), barium titanate (BaTiO$_3$), PbZrO$_3$, PbTiO$_3$, PZT, ZnO, GaAs, quartz and niobate.

The piezoelectric substrate 110 may be surface-treated with a material capable of binding to a receptor to be bound to the target biomolecule, or a material capable of forming a self-assembled monolayer ("SAM").

The IDT electrode 120 is an interface between an electric circuit and an acoustic delay line. The IDT electrode 120 may include a pair of separate IDT electrodes, as illustrated in FIG. 5. In the pair of IDT electrodes 121 and 122, one IDT electrode 121 generates a surface acoustic wave in response to an applied signal, and thus is referred to as an "input IDT electrode 121" or "transmitter." Here, the generated surface acoustic wave is transmitted to the other IDT electrode 122 by being expanded and compressed with an appropriate frequency along the surface of the substrate, and thus converted into an electrical signal by the reverse piezoelectric effect. The second IDT electrode is referred to as an "output IDT electrode 122" or "receiver."

The IDT electrode 120 may include aluminum (Al) or an Al alloy. The Al alloy may include Al as a main component, and at least one of Ti, Si, Cr, W, Fe, Ni, Co, Pb, Nb, Ta, Zn and V.

An operating principle of the SAW sensor 100 will be described. An electric signal generates a mechanical wave through the input IDT electrode 121. This wave is changed by a mechanical, chemical or electrical reaction as a receptor included in the reactive layer 130 of the surface of the SAW sensor 100 binds to a target material. In other words, an output signal of the SAW sensor 100 is changed in a center frequency, phase or signal intensity. Accordingly, the signal change is observed, thereby sensing that the target biomolecule 200 binds to the SAW sensor 100, and thus the target material can be qualitatively and quantitatively analyzed.

The receptor 300 binds to the reactive layer 130, and the target biomolecule 200 binds thereto by a selective bond. Therefore, as the change in weight occurs, a shear stress of the SAW sensor 100 excited by the IDT electrode 121 is changed. Consequently, the target material may be precisely detected when the IDT electrode 122 receives and uses the change in shear stress by measuring the change in oscillating frequency.

Detecting Method of Target Biomolecule

An embodiment of a method of detecting a target material from various biomolecules present in a sample is provided.

In one embodiment, the method includes separating biomolecules having a size same as or similar to the target biomolecule, or separating biomolecules excluding biomolecules having a size considerably different from the target biomolecule from the sample, and reacting the separated biomolecules with a reaction part of a surface of a SAW sensor 100 including a receptor 300 specifically binding to the target biomolecule 200.

According to this method, the various biomolecules present in the original sample are first separated by their sizes, and biomolecules having a size approximately similar to the target biomolecule or biomolecules other than biomolecules having a size considerably different from the target biomolecule, are subjected to analysis of whether they react or do not react with the receptor 300 using the SAW sensor 100. Thus, an error caused by non-specific binding can be reduced, the sensitivity and reproducibility can be increased, and as a large amount of reaction inhibitors (e.g., antibodies) in a sample are removed, a reaction rate on a surface of the SAW sensor 100 can be improved, leading to improvement in sensitivity.

The separation of the biomolecules by size may be performed by electrophoresis. During the separation by electrophoresis, it is necessary to prevent dilution of the sample by a buffer or modification of the sample caused by the pH change by current application. To this end, the above-described SAW sensor 100 may be used.

The separated biomolecules may have a size similar to the target biomolecule, for example, approximately ±50%, ±40%, ±30%, ±20% or ±10% or less of the target biomolecule 200.

The separated biomolecules may be biomolecules excluding biomolecules having a size considerably different from the target biomolecule, for example, a size of approximately ±500%, ±400%, ±300%, ±200% or ±100% or more of the target biomolecule. Hereinafter, the disclosure will be described with reference to an Experimental Example.

For the Experimental Example, in the SAW sensor shown in FIG. 1, native electrophoresis buffers including 3.0 grams (g) Tris base and 14.4 g glycine in water (pH 8.3) were contained in a first chamber 10 and a second chamber 20, respectively. A polyacrylamide gel having about 6%, about 8% and about 10% concentration gradients in a migration direction of a sample, as an electrophoresis gel, was contained in a channel 31 defined by a channel chamber 30. As a first blocking wall 40 and a second blocking wall 50, commercially available ion exchanging layers were used.

As a sample, 1 micrograms per milliliter (µg/ml) prostate specific antigen ("PSA") spiked human serum was input into a sample chamber 60. The molecular weight (Mw) of PSA is 34,000, and the volume of the sample was 100 microliter (µl). Electrophoresis was performed at room temperature with a voltage of 100 volts (V), and the separation was performed for about 100 minutes. When materials having a size similar to the target molecule, PSA, passed through the electrophoresis gel, the electricity was interrupted. Afterwards, the sample was transferred to the SAW sensor 100 in which an anti-PSA antibody, as a receptor 300, was attached to a reaction part of the SAW sensor 100 to react with the sample.

For comparison, the same sample not subjected to electrophoresis reacted with a SAW sensor 100 to which bovine serum albumin ("BSA") was attached (Comparative Example 1).

As a result, as shown in Table 1, in Comparative Example 1 in which the electrophoresis was not performed, impurities were adsorbed to BSA, and thus a frequency was considerably changed. However, in the case of the Experimental Example in which electrophoresis was performed, it can be noted that a noise was minimized, and thus a frequency variation had a positive value due to an antigen-antibody reaction.

TABLE 1

|  | ΔFrequency (Hz) |
| --- | --- |
| Electrophoresis was performed (Experimental Example) | 900 |
| Electrophoresis was not performed (Comparative Example 1) | −3210 |

While embodiments have been disclosed herein, it should be understood that other variations may be possible. Such variations are not to be regarded as a departure from the spirit and scope of embodiments of the present application, and all such modifications as would be obvious to one skilled in the art are intended to be included within the scope of the following claims.

What is claimed is:

1. A surface acoustic wave sensor device comprising:
   a surface acoustic wave sensor comprising a receptor, wherein the receptor binds to a target biomolecule of a sample; and an isolation component connected to the surface wave sensor, wherein the isolation component separates biomolecules having a size the same as or similar to the target biomolecule or separates biomolecules by excluding biomolecules having a size considerably different from the target biomolecule, through an electrophoresis process; and wherein the isolation component comprises a first chamber to contain a first buffer, and a first electrode positioned to contact the first buffer;

a second chamber to contain a second buffer, and a second electrode positioned to contact the second buffer;

a channel fluidly connecting the first and second chambers;

a blocking wall at an end of the channel and between the channel and the first chamber or between the channel and the second chamber, wherein the blocking wall comprises a material that passes a current but does not pass ions and/or gases generated from the buffer; and a sample chamber at an entry of the channel and into which a sample is loaded.

2. The device of claim 1, wherein the electrophoresis process is selected from the group consisting of gel electrophoresis, capillary electrophoresis, isoelectric focusing electrophoresis, and isotachophoresis.

3. The device of claim 2, wherein the isolation component further comprises:

a third chamber at an exit of the channel and to which the biomolecules passed through the channel are transferred, wherein the surface acoustic wave sensor is connected to the third chamber of the isolation component.

4. The device of claim 3, wherein the isolation component further comprises:

a disposal chamber;

an upper channel connected to the third chamber and the disposal chamber;

a lower channel connected to the third chamber and the surface acoustic wave sensor, and a pump connected to an end of the upper channel and an end of the lower channel.

5. The device of claim 3, wherein the channel is a gel tube or capillary filled with electrophoresis gel.

6. The device of claim 3, comprising a plurality of channels, wherein each of the channels is a gel tube or capillary filled with electrophoresis gel.

7. The device of claim 6, wherein the channels are different from each other based on the sample loaded, size or length of the channel, composition or concentration of the electrophoresis gel, or coating material of the channel.

8. The device of claim 3, further comprising an electric sensor connected to the third chamber, wherein the electric sensor senses biomolecules.

9. A method of detecting a target biomolecule, the method comprising:

separating from a sample biomolecules having a size the same as or similar to a target biomolecule, or separating from the sample biomolecules by excluding biomolecules having a size considerably different from a target biomolecule, from a sample by means of an electrophoresis; and reacting the separated biomolecules with a reactive part on a surface of a surface acoustic wave sensor, the reactive part having a receptor specifically binding to the target biomolecule, wherein the separating biomolecules is performed by an isolation component connected to the surface acoustic wave sensor, the isolation component comprising a first chamber to contain a first buffer, and a first electrode positioned to contact the first buffer;

a second chamber to contain a second buffer, and a second electrode positioned to contact the second buffer;

a channel fluidly connecting the first and second chambers;

a blocking wall at an end of the channel and between the channel and the first chamber or between the channel and the second chamber, wherein the blocking wall comprises a material that passes a current but does not pass ions and/or gases generated from the buffer; and a sample chamber at an entry of the channel and into which the sample is loaded.

10. The method of claim 9, wherein the isolation component further comprises:

a third chamber at an exit of the channel and to which the biomolecules passed through the channel are transferred, wherein the surface acoustic wave sensor is connected to the third chamber of the isolation component.

11. The method of claim 10, wherein the isolation component further comprises:

a disposal chamber;

an upper channel connected to the third chamber and the disposal chamber;

a lower channel connected to the third chamber and the surface acoustic wave sensor, and a pump connected to an end of the upper channel and an end of the lower channel.

12. The method of claim 10, wherein the channel is a gel tube or capillary filled with electrophoresis gel.

13. The method of claim 10, wherein the device comprises a plurality of channels, wherein each of the channels is a gel tube or capillary filled with electrophoresis gel.

14. The method of claim 13, wherein the channels are different from each other based on the sample loaded, size or length of the channel, composition or concentration of the electrophoresis gel, or coating material of the channel.

15. The method of claim 10, further comprising an electric sensor connected to the third chamber, wherein the electric sensor senses biomolecules.

16. The method of claim 9, wherein the electrophoresis process is gel electrophoresis, capillary electrophoresis, isoelectric focusing electrophoresis, and isotachophoresis.

17. The device of claim 1, comprising a blocking wall at an end of the channel and between the channel and the first chamber, and a blocking wall at an opposite end of the channel and between the channel and the second chamber, wherein the blocking walls each comprise a material that passes a current but does not pass ions and/or gases generated from the buffer.

18. The method of claim 9, wherein the isolation device comprises a blocking wall at an end of the channel and between the channel and the first chamber, and a blocking wall at an opposite end of the channel and between the channel and the second chamber, wherein the blocking walls each comprise a material that passes a current but does not pass ions and/or gases generated from the buffer.

\* \* \* \* \*